United States Patent
Kleiber et al.

(10) Patent No.: US 9,422,220 B2
(45) Date of Patent: Aug. 23, 2016

(54) METHOD FOR PURIFYING CARBOXYLIC ACIDS FROM FERMENTATION BROTHS

(71) Applicant: THYSSENKRUPP INDUSTRIAL SOLUTIONS AG, Essen (DE)

(72) Inventors: Michael Kleiber, Hattersheim (DE); Ulrike Gnabs, Kelkheim (DE); Joachim Schulze, Soest (DE); Shashank Ghanegaonkar, Leipzig (DE); Helmut Gehrke, Bergkamen (DE); Marcel Gawenda, Sassenberg (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 14/759,141

(22) PCT Filed: Dec. 20, 2013

(86) PCT No.: PCT/EP2013/003892
§ 371 (c)(1),
(2) Date: Jul. 2, 2015

(87) PCT Pub. No.: WO2014/106532
PCT Pub. Date: Jul. 10, 2014

(65) Prior Publication Data
US 2015/0344397 A1    Dec. 3, 2015

(30) Foreign Application Priority Data

Jan. 3, 2013 (DE) .......................... 10 2013 000 027

(51) Int. Cl.
| | |
|---|---|
| *C07C 51/43* | (2006.01) |
| *C07C 51/47* | (2006.01) |
| *B01D 9/00* | (2006.01) |
| *B01D 1/00* | (2006.01) |
| *B01D 15/02* | (2006.01) |
| *B01D 61/02* | (2006.01) |
| *C07C 51/44* | (2006.01) |

(52) U.S. Cl.
CPC . *C07C 51/44* (2013.01); *B01D 1/00* (2013.01); *B01D 9/00* (2013.01); *B01D 15/02* (2013.01); *B01D 61/025* (2013.01); *C07C 51/43* (2013.01); *C07C 51/47* (2013.01); *B01D 2311/02* (2013.01)

(58) Field of Classification Search
CPC ........ C07C 51/43; C07C 51/44; C07C 51/47; B01D 9/00; B01D 15/02; B01D 61/025; B01D 1/00; B01D 2311/02
See application file for complete search history.

(56) References Cited

U.S. PATENT DOCUMENTS

| | | | |
|---|---|---|---|
| 8,957,249 B2 * | 2/2015 | Tietz ......................... | C12P 7/46 562/513 |
| 9,233,906 B2 * | 1/2016 | Gerberding ............. | C07C 51/43 |

FOREIGN PATENT DOCUMENTS

| | | |
|---|---|---|
| DE | 102010025167 A1 | 12/2011 |
| WO | 2011082378 A2 | 7/2011 |

OTHER PUBLICATIONS

PCT/EP2013/003892, International Search Report and Written Opinion, dated Jul. 7, 2014, 10 pages.

* cited by examiner

*Primary Examiner* — Shailendra Kumar
(74) *Attorney, Agent, or Firm* — Lathrop & Gage LLP

(57) ABSTRACT

Method and devices for separating and purifying carboxylic acids from fermentation broths comprising carboxylic acid ammonium salts are disclosed herein. The method includes (a) removing biomass and any solids present from the fermentation broth; (b) preparing a solution comprising the desired carboxylic acid and an additional solution comprising ammonium salts, by carrying out simulated moving bed chromatography (SMB); (c) ultra-purifying the solution comprising the desired carboxylic acid from method step (b); (d) concentrating the purified carboxylic acid solution from method step (c); (e) crystallizing the concentrated carboxylic acid solution from method step (d); and (f) concentrating the additional solution comprising ammonium salts from method step (b). A combination of reverse osmosis and evaporation is carried out in method steps (d) and (f), and the vapor from the evaporation of method step (f) is passed into the evaporation of method step (d).

20 Claims, No Drawings

METHOD FOR PURIFYING CARBOXYLIC ACIDS FROM FERMENTATION BROTHS

CROSS-REFERENCE TO RELATED APPLICATIONS

This application is the national phase of, and claims priority to, International Patent Application No. PCT/EP2013/003892, filed Dec. 20, 2013, which designated the U.S. and which claims priority to German Application No. 102013000027.0, filed Jan. 3, 2013. These applications are each incorporated by reference herein in their entireties.

BACKGROUND

1. Field of the Invention

The invention relates to a method for purifying carboxylic acids from fermentation broths, and also a device for carrying out the method according to the invention. The isolation of carboxylic acids, which cannot be separated by distillation or only with difficulty, proves to be very complex.

2. Description of the Related Art

The decisive factor for the industrial use of carboxylic acids, which are generated by fermentation of carbohydrate-containing substrates by various microorganisms, is the economic viability and efficiency of the separation and purification of the lactic acid from these aqueous fermentation solutions, which also comprise, in addition to the carboxylic acid or the carboxylic acid salts, further organic acids, other by-products of the fermentation, microorganisms and constituents thereof and also residues of the substrates such as sugar. These impurities impair the subsequent processing of the carboxylic acids generated. For example, lactic acid is polymerized to polylactic acid in order to produce biologically degradable plastics. In this case, an extremely pure monomer must be used in order to attain a high degree of polymerization of the lactic acid. This has long been known and appears, for example, in J. Dahlmann et al, British Polymer Journal, Vol. 23 (1990), pp 235-240.

The same is known for succinic acid for example. The qualities of the succinic acid produced may be differentiated by subdivision into a technical grade having a succinic acid content of at least 97% by mass and a succinic acid specifically suitable for use for polymerization (polymer grade) having a content of at least 99.5% by mass.

A number of patents describe the production of succinic acid from fermentation solutions, including:

- extractive processes using extraction agents such as tributylamines, trialkylamines, olefins, various alcohols and aromatic hydrocarbons;
- processes using calcium hydroxide and sulfuric acid, in which gypsum occurs as by-product;
- processes using electrodialysis;
- thermal methods such as fractional distillation or thermal stepped chromatography;
- high pressure extraction using $CO_2$; and
- membrane methods such as reverse osmosis and other filtration processes;

wherein coupling of these processes and supplementation by additional steps corresponding to the prior art are also discussed. Such methods are described, inter alia, in patent specifications DE 69821951 T2; DE 69015233 T2; DE 69015019 T2; DE 69006555 T2; DE 69015019; DE19939630C2; DE 60028958T2; and DE 10 2004 026152 A1.

Numerous methods relating to the purification of lactic acid are also known. For example, it is taught in a number of patents to use distillation for purifying lactic acid from aqueous solutions. Such a method is made use of in EP 0986532 B2. DE 10 2007 045 701 B3 discloses a combined extraction with linear n-trioctylamine (TOA) and distillation. Other possibilities known from the literature are electrodialysis or esterification with an alcohol after which distillation and then hydrolysis of the ester formed are likewise carried out. These methods are extremely cost-intensive. Distillation also has the disadvantage that a part of the carbohydrates are also always co-extracted which leads to a deterioration in the yield of the overall process and makes it difficult to isolate the product.

Processes using calcium hydroxide and sulfuric acid are also known in which gypsum occurs as by-product in large amounts. In this context, it was also found that lactic acid can be isolated by chromatographic methods from, for example, a fermentation broth acidified with sulfuric acid, which still comprises ammonium and sulfate ions in addition to free lactic acid. By way of example, DE 69815369 T2 describes, inter alia, the removal of lactic acid from aqueous mixtures by adsorption on a solid adsorbent, a solid adsorbent preferably being used here which adsorbs lactic acid as opposed to lactate. In particular, it is possible to use weak anion exchangers for the isolation of lactic acid according to the above documents. DE 10 2009 019 248 A1 further describes chromatographic methods for purifying organic acids, especially lactic acid, by carrying out simulated moving bed chromatography.

WO 2006/124633 A1 describes a process for preparing ammonium lactate by fermentation. The ammonium salt of lactic acid is formed in the fermentation which may be separated from the fermentation solution, for example, by extraction. The ammonium salt can be very readily cleaved in a subsequent step using weak acids or carbon dioxide. The free lactic acid is thus obtained which can then be purified, for example, by distillation.

WO99/19290 describes a lactic acid fermentation with subsequent filtration and extraction, where the extraction can be an adsorption. In this case, the type of interaction in the solid phase adsorption is not disclosed. A similar method is disclosed in WO93/06226, in which the adsorption solid phase is equipped with tertiary amino groups and the rate of production of free acid is thereby increased. EP0135728 also teaches the isolation of enzymatically generated carboxylic acids via adsorbents which are equipped with tertiary amino groups. The fermentation is carried out in this case by cells immobilized on columns.

DE102010025167A1 discloses a method for separating, recovering and purifying succinic acid. Separation of the biomass from the fermentation broth in this case is achieved in two successive steps. The dicarboxylic acid solution is then separated from the biomass-free fermentation broth by simulated moving bed chromatography, followed by ultra-purification and a multi-stage evaporation and crystallization. A disadvantage of this method is the high energy expenditure caused by the multi-stage evaporation of the dicarboxylic acid solution.

WO2011082378A2 teaches the purification of succinic acid from a fermentation broth comprising ammonium succinate. Ion exchange columns are used to separate the ammonium succinate from the fermentation broth and to generate succinic acid. In this case, ammonium sulfate is obtained in the raffinate and succinic acid in the extract. The raffinate is subjected to a crystallization, for which purpose it is concentrated. The concentration of the raffinate, i.e. of the ammonium sulfate, is carried out by reverse osmosis and/or evaporation. This step is generally known. The workup of the ammonium sulfate is essential for the economic viability of the preparation of succinic acid by fermentation, since in the conversion of ammonium succinate to succinic acid from the fermentation broth, about one and a half times the amount of ammonium sulfate is obtained.

A disadvantage of many processes, therefore, is that the practical implementation of the methods is associated with considerable technical and energy expenditure.

SUMMARY OF THE INVENTION

Disclosed herein is an energetically favorable overall process for separating and purifying carboxylic acids from fermentation broths, wherein known disadvantages of other methods can be avoided.

DETAILED DESCRIPTION

Disclosed herein, in one embodiment of the invention, is a method for separating and purifying carboxylic acids from fermentation broths, wherein the method comprises the steps of:
- a. removing biomass and any solids present from the fermentation broth;
- b. preparing a solution comprising the desired carboxylic acid and an additional solution comprising ammonium salts, by acidifying the biomass-free fermentation broth with concentrated sulfuric acid and subjecting it to simulated moving bed chromatography (SMB);
- c. ultra-purifying the solution comprising the desired carboxylic acid from method step b);
- d. concentrating the purified carboxylic acid solution from method step c);
- e. crystallizing the concentrated carboxylic acid solution from method step d); and
- f. concentrating the additional solution comprising ammonium salts from method step b).

In the method steps d) and f), a combination of reverse osmosis and evaporation may be carried out and the vapor from the evaporation of method step f) may be passed into the evaporation of method step d).

The conversion and recovery of the ammonium salts is essential for the economic viability of the preparation of succinic acid by fermentation.

In one embodiment, method step f) is designed such that in method step d), under normal operation, no fresh vapor is to be supplied or 1 to 10 t of fresh vapor per t of carboxylic acid product is to be supplied, particularly preferably 1.5 to 4 t of fresh vapor per t of carboxylic acid product is to be supplied. Normal operation here means the operation after power-up of the plant and implies no disruptions to the operational procedure.

In a further embodiment, the removal of the biomass from the fermentation broth in method step a) is effected by precoat filtration and/or microfiltration and/or ultrafiltration and the biomass removed in method step a) is fed back again into the fermenter. In this case, the temperature and pH correspond to the values of the fermentation since it has been found that autolysis of the biomass is accelerated by inactivation of the biomass by increasing the temperature and lowering the pH by addition of acid and more lysis products are released into the fermentation broth. The time between completion of the fermentation and removal of the biomass must also be kept as short as possible and not exceed 2 h and preferably be less than 1-2 h. The biomass concentration in the filtrate should not exceed 1 g/l. The quality of the final product may be positively influenced by this process.

Numerous microorganisms can be used for the fermentation itself, including bacteria, yeasts and fungi. The fermentation broth may also include various recycling streams from the overall process.

The filtrate from the precoat filtration or microfiltration may also optionally be fed to a single- or two-stage ultrafiltration. Here, residual biomass components, insoluble solids and higher molecular weight compounds are removed. Membranes having a cut-off of ≤10 kDa were determined as optimal between product quality and flux rates of the membranes. The temperature of the liquid media should be ≥ approximately 30° C. due to the solubility coefficient of ammonium succinate in water. The retentate is fed back to the precoat filtration or microfiltration or alternatively collected and used as starting material for the generation of technical grade dicarboxylic acids and the permeate is supplied for further treatment.

The dicarboxylic acid is present in the permeate of method step a) in the form of its salt—in the case of succinic acid, for example, in the form of ammonium succinate. For conversion to the carboxylic acid, concentrated sulfuric acid is added and mixed in and this leads to a lowering of the pH of the solution to values between 2.2 and 2.4. In this case, ammonium sulfate is formed in a stoichiometric ratio. To avoid undesired precipitation, this process step may be conducted at temperatures between approximately 30° C. and approximately 60° C. and preferably in a range between approximately 30° C. and approximately 40° C. This pre-purified solution is available for separating and purifying the dicarboxylic acid. The acidification is also optionally carried out in two stages by carrying out the first acidification before method step a) and the second acidification after method step a).

The separation of the acidic permeate of the ultrafiltration may be carried out by simulated moving bed (SMB) chromatography. This is a particularly efficient variant of high performance liquid chromatography, wherein a large number of theoretical plates is achieved by the sequence of several separation columns linked to one another by valves in an infinite loop and the selectivity of the chromatography is considerably improved. Cation exchangers and anion exchangers are used as stationary phase. After applying the solution, the dicarboxylic acid is bound to the stationary phase and is eluted from the system after repeated washing of the undesired constituents of the solution and is discharged as a separate extract. Demineralized water and/or vapor condensate are used as eluent. It is also possible to use the permeate from the reverse osmosis as eluent. The economic viability of the overall process can be further improved by recirculating the water.

It could be shown that more than 95% of the dicarboxylic acid present in the permeate from the ultrafiltration can be obtained in the extract, wherein the ratio between the permeate of the ultrafiltration and the eluent varies in the range between 1:1.5 and 1:2.5 and eight anion exchange columns connected in an infinite loop were used. The extract comprises only low amounts of ammonium sulfate, acetic acid and colorants from the fermenter broth. The eluted raffinate comprises at most 1 g/l dicarboxylic acids and also ammonium sulfate and accompanying salts from the fermentation such as phosphates, nitrates and chlorides.

In carrying out the SMB of method step b), the following conditions may be maintained:
- the addition of the permeate from the filtration from method step a) and of an eluent is carried out continuously in a ratio of permeate:eluent of approximately 1:1.5 to 1:2.5;

the carboxylic acid binds to a stationary phase of the SMB, wherein said stationary phase is composed of a cation exchanger and/or an anion exchanger;

the extract comprising the carboxylic acid and the raffinate, having a dicarboxylic acid content of ≤1 g/l, are collected separately from each other; and the efficiency of the recovery of carboxylic acid from the permeate of the filtration from method step a) is ≥ approximately 95%.

To prepare high purity dicarboxylic acid (polymer grade), ultra-purification of the extract from the simulated moving bed chromatography may be carried out, wherein the membranes have a separation size of 100 to 400 Da. It could be shown that nanofiltration using a cut-off of 200 Da gives good results. The process is operated such that the retentate of the nanofiltration is not more than 10% of the total throughput. The retentate still comprises acetic acid and colorants in addition to the carboxylic acid and can be added to the starting material for generating technical grade carboxylic acid.

Depending on the quality of the raw materials used for the fermentation and the process control in the fermentation, an additional ultra-purification of the permeate from the upstream nanofiltration or the extract from the SMB chromatography is carried out, due to residues of colorants and accompanying substances still present. In this case, an ultra-purification by activated carbon filtration and/or ion exchange is conducted downstream. Cation and/or anion exchangers are useful as ion exchange resins depending on the chemical analysis of the impurities.

In a further embodiment, at least one or more stages for the reverse osmosis are combined with at least one or more method steps for the evaporation in method step d).

The preparation of the carboxylic acid product—both in technical and polymer grade quality—is carried out by crystallization. It has been found that the parameters of the process control have considerable impact on the product quality.

To achieve a technical grade having a carboxylic acid content of ≥ approximately 97% by mass, it is sufficient if method step d) and e) are carried out in a single pass through these method steps. The reverse osmosis and evaporation are conducted up to a concentration of 30 to 50% by mass. The essential parameter for product quality was found to be the temperature gradient applied to the cooling of the solution during the crystallization. Accordingly, the cooling should take place in steps of 3-8° C./min and preferably in steps of 3-5° C./min. The crystals formed are then separated from the mother liquor by separation, washed with hot water at 40° C. and returned to the mother liquor before the evaporation. The crystals are dried after the separation.

To achieve a polymer grade quality of the carboxylic acid having a content of ≥ approximately 99.5% by mass, it has been found that the temperature should be in the range from about 70° C. to about 80° C. and the solution must be adjusted to a concentration of about 50±5% by mass. The temperature gradient during the cooling of the solution was found to be essential for the quality of the crystals. Accordingly, cooling was applied in steps of 1° C. to 5° C./h. Crystals are thereby generated in polymer grade quality which are separated by separation and dried. The mother liquor can be recycled. If necessary after the separation, the crystals can be dissolved in demineralized water and/or vapor condensate and the crystallization and separation step repeated.

The crystals of the carboxylic acid after the crystallization are advantageously separated off by separation, wherein the resulting mother liquor is fed back to before the evaporation and the crystals are subsequently dried.

In order to make the process economically effective, the ammonium salts from method step c) are concentrated in method step f).

The retentates of the various filtrations from method step c) are optionally combined and serve as starting solutions for preparing a carboxylic acid of technical grade quality. The dried crystals are packaged for further use.

The method according to the invention may be advantageous for purifying carboxylic acids selected from the group comprising hydroxycarboxylic acids and dicarboxylic acids, and are preferably selected from the group comprising malic acid, glycolic acid, isocitric acid, mandelic acid, lactic acid, tartronic acid, tartaric acid, citric acid, β-hydroxybutyric acid, mevalonic acid, salicylic acid, oxalic acid, maleic acid, succinic acid, glutaric acid, adipic acid, pimelic acid, suberic acid, fumaric acid and itaconic acid.

The present invention additionally includes one or more filtration devices for removing biomass and any solids present from the fermentation broth. The devices may be used for carrying out the following:

a) a method step for simulated moving bed chromatography (SMB) after acidification, wherein a solution comprising the desired carboxylic acid and an additional solution comprising ammonium salts is produced;

b) a method step for ultra-purifying the solution comprising the desired carboxylic acid from method step a);

c) a method step for concentrating the purified carboxylic acid solution from method step b);

d) a method step for crystallizing the concentrated carboxylic acid solution from method step c); and e) a method step for concentrating the additional solution comprising ammonium salts from method step a).

Method steps c) and e) comprise a combination of one or more devices for reverse osmosis and one or more devices for evaporation, and connections are in place to transfer the vapor from the evaporation of method step e) to the evaporation of method step c).

In one embodiment of the device according to the invention, in method step d) plant components are designed for generating fresh vapor with a fresh vapor generation of 1 to 10 t of fresh vapor per t of carboxylic acid product, and are particularly designed for a fresh vapor generation of 1.5 to 4 t of fresh vapor per t of carboxylic acid product.

It is also advantageous if connections are in place to transfer the permeate from the reverse osmosis into the simulated moving bed chromatography of method step b). In this manner, the overall process can be made even more economical.

EXAMPLE 1

A fermenter broth comprising ammonium succinate was pre-purified by filtration according to the description. After converting the ammonium salt into the acid form of succinic acid, the solution was separated by simulated moving bed chromatography into 5.7 l of extract and 6.6 l of raffinate. In this case, a total of 8 separation columns having a strongly acidic cation exchanger were connected in an infinite loop. At a permeate/eluent ratio of 2.4, the coefficient of succinic acid recovery was 99.9%. The sulfate concentration in the extract was 238 mg/l and in the raffinate 35.709 mg/l, whereby a sulfate elimination of 99.4% was achieved.

EXAMPLE 2

A fermenter broth comprising ammonium succinate was pre-purified by filtration according to the description. After converting the ammonium salt into the acid form of succinic acid, the solution was separated by simulated moving bed chromatography into 5.3 l of extract and 6.1 l of raffinate. In this case, a total of 8 separation columns having a strongly acidic cation exchanger were connected in an infinite loop. At a permeate/eluent ratio of 2.2, the coefficient of succinic acid recovery was 99.8%. A sulfate elimination of 97.9% was achieved.

EXAMPLE 3

An extract from the simulated moving bed chromatography comprising the succinic acid was subjected to an ultra-purification by nanofiltration using a cut-off of 200 Da. In the extract, contents of 44.8 g/l succinic acid and 698 mg/l sulfates were analyzed. The filtered extract was concentrated, crystallized and analyzed. The crystals had a succinic acid content of 1.031 g/l and a content of residual sulfates of 21.9 mg/l and chlorides of 13.8 mg/l. The color of the crystals was "white".

EXAMPLE 4

An extract from the simulated moving bed chromatography comprising the succinic acid with a content of 44.77 g/l succinic acid and 699 mg/l sulfates was subjected to an ultra-purification by nanofiltration using a cut-off of 200 Da and subsequently subjected to activated carbon filtration. The crystals generated from the ultra-purification had a content of succinic acid of 1.065 g/l and residual sulfates of 35.3 mg/l and also 9.5 mg/l chlorides. The color of the crystals was "pure white".

EXAMPLE 5

An extract from the simulated moving bed chromatography comprising the succinic acid was subjected to an ultra-purification by ion exchange. The extract had a content of 44.8 g/l succinic acid, 699 mg/l sulfates and 1.88 mg/l chlorides. The crystals generated from the ultra-purified solution had a content of succinic acid of 967 g/l succinic acid, 37.6 mg/l sulfates and 0.92 mg/l chlorides. The color of the crystals was "white".

EXAMPLE 6

Raffinate obtained analogously to Example 2 comprising ammonium sulfate at a concentration of 5% was subjected to reverse osmosis and evaporation. After the reverse osmosis, the concentration of the ammonium sulfate in the raffinate is 12%. This solution was then subjected to a further concentration to 40% by evaporation. The concentrated solution comprised an ammonium sulfate content of 40%. For the evaporation, 2.1 t of vapor were fed in per t of ammonium sulfate. Vapor exiting from the evaporation unit was passed into the evaporation unit for concentrating the extract comprising succinic acid (ca. 2.1 t of vapor per t of succinic acid) and was further used there. By coupling with reverse osmosis, no additional fresh vapor has to be fed to the evaporation unit of the carboxylic acid.

Advantages of the method according to the invention may be recognized in that, by combining reverse osmosis and evaporation in accordance with the invention and the further processing of the vapor from the raffinate concentration of method step f), considerable savings of vapor and thereby energy are possible, and the method of purifying carboxylic acids from fermentation broths is made considerably more economical than methods from the prior art.

The described embodiment of the invention may self-evidently also be modified in a variety of aspects, without departing from the basic concept.

The invention claimed is:

1. A method for separating and purifying carboxylic acids from fermentation broths comprising carboxylic acid ammonium salts, the method comprising the steps of:
    a) removing biomass and any solids present from the fermentation broth;
    b) preparing a solution comprising the desired carboxylic acid and an additional solution comprising ammonium salts comprising the steps of:
        b1) acidifying the biomass-free fermentation broth with concentrated sulfuric acid; and
        b2) subjecting the product of step b1) to simulated moving bed chromatography (SMB);
    c) ultra-purifying the solution comprising the desired carboxylic acid from step b);
    d) concentrating the purified carboxylic acid solution from step c);
    e) crystallizing the concentrated carboxylic acid solution from step d); and
    f) concentrating the additional solution comprising ammonium salts from step b);
    wherein:
        in steps d) and f), a combination of reverse osmosis and evaporation is carried out; and
        the vapor from the evaporation of step f) is passed into the evaporation of step d).

2. The method of claim 1, wherein step f) is designed such that in step d), under normal operation, no fresh vapor is supplied.

3. The method of claim 1, wherein step f) is designed such that in step d), under normal operation, 1 to 10 t of fresh vapor per t of carboxylic acid product is supplied.

4. The method of claim 1, wherein step f) is designed such that in step d), under normal operation, 1.5 to 4 t of fresh vapor per t of carboxylic acid product is supplied.

5. The method of claim 1, wherein the permeate resulting from the reverse osmosis is used as eluent in step b).

6. The method of claim 1, wherein:
    the removal of the biomass from the fermentation broth in step a) is effected by at least one of: precoat filtration, microfiltration, and ultrafiltration; and
    the biomass removed in step a) is fed back into the fermenter.

7. The method of claim 6, wherein the removal of the biomass from the fermentation broth in step a) is carried out without lowering the pH and without thermal inactivation.

8. The method of claim 7, wherein, in step a), the time between completion of the fermentation and the removal of the biomass is less than 2 hours.

9. The method of claim 7, wherein, in step a), the time between completion of the fermentation and the removal of the biomass is less than 1 hour.

10. The method of claim 8, wherein, in step a), the biomass concentration in the filtrate is not higher than 1 g/l.

11. The method of claim 10, wherein:
    the permeate from the filtration of step a) is acidified with concentrated sulfuric acid to a pH of 2.2 to 2.4; and
    wherein the temperature of the acidified permeate of the ultrafiltration is maintained in a range between 30° C. and 60° C.

12. The method of claim 11, wherein the temperature of the acidified permeate of the ultrafiltration is maintained in a range between 30° C. and 40° C.

13. The method of claim 1, wherein, in step b):
the addition of the permeate from the filtration from step a) and of an eluent is carried out continuously in a permeate:eluent ratio of between 1:1.5 and 1:2.5;
the carboxylic acid binds to a stationary phase of the SMB, wherein said stationary phase is composed of at least one of a cation exchanger and an anion exchanger;
the extract comprising the carboxylic acid and the raffinate, having a dicarboxylic acid content of ≤1 g/l, are collected separately from each other; and
the efficiency of the recovery of carboxylic acid from the permeate of the filtration from step a) is ≥95%.

14. The method of claim 1, wherein:
the extract from the SMB chromatography from step b) is subjected to a nanofiltration in step c) wherein the membranes have a cut-off of between 100 and 400 Da; and
at least one of ultra-purification by activated carbon filtration, cation exchange, and anion exchange is carried out in step c).

15. The method of claim 14, wherein at least one or more steps for the reverse osmosis are combined with at least one or more steps for the evaporation in step d).

16. The method of claim 1, wherein the carboxylic acids to be separated and purified are selected from the group consisting of: hydroxycarboxylic acids and dicarboxylic acids.

17. The method of claim 1, wherein the carboxylic acids to be separated and purified are selected from the group consisting of: malic acid, glycolic acid, isocitric acid, mandelic acid, lactic acid, tartronic acid, tartaric acid, citric acid, β-hydroxybutyric acid, mevalonic acid, salicylic acid, oxalic acid, maleic acid, succinic acid, glutaric acid, adipic acid, pimelic acid, suberic acid, fumaric acid and itaconic acid.

18. A device for carrying out a method for separating and purifying carboxylic acids from fermentation broths, comprising one or more filtration devices for removing biomass and any solids present from the fermentation broth, wherein the device facilitates:
a) a step for simulated moving bed chromatography (SMB) after acidification, wherein a solution comprising the desired carboxylic acid and an additional solution comprising ammonium salts is produced;
b) a step for ultra-purifying the solution comprising the desired carboxylic acid from step a);
c) a step for concentrating the purified carboxylic acid solution from step b);
d) a step for crystallizing the concentrated carboxylic acid solution from step c); and
e) a step for concentrating the additional solution comprising ammonium salts from step a);
wherein
steps c) and e) comprise a combination of one or more devices for reverse osmosis and one or more devices for evaporation; and
connections are in place to transfer the vapor from the evaporation of step e) to the evaporation of step c).

19. The device of claim 18, wherein, in step c), plant components are designed for generating fresh vapor with a fresh vapor generation of 1.5 to 4 t of fresh vapor per t of carboxylic acid product.

20. The device of claim 19, wherein connections are in place to transfer the permeate from the reverse osmosis into the simulated moving bed chromatography of step a).

* * * * *